US009027852B2

(12) United States Patent
Fang et al.

(10) Patent No.: US 9,027,852 B2
(45) Date of Patent: May 12, 2015

(54) CONSTANT QUANTITY CONTROL NEBULIZATION DEVICE

(71) Applicant: Micro Base Technology Corporation, Bade (TW)

(72) Inventors: Tun-Ying Fang, Bade (TW); Tai-Shuan Lin, Bade (TW); Chia-Lun Hsieh, Bade (TW); Shao-Ming Yang, Bade (TW); Yu-De Su, Bade (TW); Chi-Shan Hung, Bade (TW)

(73) Assignee: Micro Base Technology Corporation, Taoyuan County (TW)

( * ) Notice: Subject to any disclaimer, the term of this patent is extended or adjusted under 35 U.S.C. 154(b) by 309 days.

(21) Appl. No.: 13/845,096

(22) Filed: Mar. 18, 2013

(65) Prior Publication Data

US 2014/0166776 A1    Jun. 19, 2014

(30) Foreign Application Priority Data

Dec. 14, 2012  (TW) ............................... 101224273 U

(51) Int. Cl.
| | |
|---|---|
| *A61M 11/06* | (2006.01) |
| *B05B 17/00* | (2006.01) |
| *A61M 11/00* | (2006.01) |
| *B05B 17/06* | (2006.01) |
| *B05B 11/00* | (2006.01) |

(52) U.S. Cl.
CPC .......... *B05B 17/0646* (2013.01); *A61M 11/005* (2013.01); *B05B 11/0054* (2013.01); *B05B 17/0638* (2013.01); *B05B 17/0676* (2013.01)

(58) Field of Classification Search
CPC .......... B05B 12/14; B05B 11/30; B05B 7/24; B05B 11/3042; B05B 7/2491
USPC .......................... 239/338, 337, 309, 436, 437
See application file for complete search history.

(56) References Cited

U.S. PATENT DOCUMENTS

| | | | | |
|---|---|---|---|---|
| 5,533,501 | A * | 7/1996 | Denyer ..................... | 128/200.21 |
| 5,964,416 | A * | 10/1999 | Jaeger et al. .................. | 239/333 |
| 2002/0189611 | A1 * | 12/2002 | Greenwood et al. ..... | 128/200.23 |
| 2009/0212133 | A1 * | 8/2009 | Collins, Jr. .................... | 239/338 |
| 2010/0222752 | A1 * | 9/2010 | Collins et al. ................. | 604/296 |
| 2011/0011899 | A1 * | 1/2011 | Yeates ........................... | 222/566 |

* cited by examiner

*Primary Examiner* — Davis Hwu
(74) *Attorney, Agent, or Firm* — Leong C. Lei

(57) ABSTRACT

Disclosed is a constant quantity control nebulization device including a main body, a nebulization module, a fixing plate and a rotary ring, and the device is installed to a container that contains a liquid to be nebulized. A first liquid storage space with a predetermined volume is defined at the top of the main body, and the nebulization module is installed in the main body and interconnected to the first liquid storage space, and the fixing plate is fixed onto the main body and has a first through hole, the rotary ring is sheathed on the top of the main body and axially coupled to the fixing plate, and the rotary ring has a second through hole corresponding to the first through hole. The consumption of the liquid to be nebulized can be controlled by rotating the rotary ring to improve the convenience of operation significantly.

17 Claims, 5 Drawing Sheets

CONSTANT QUANTITY CONTROL NEBULIZATION DEVICE

CROSS-REFERENCE TO RELATED APPLICATIONS

This non-provisional application claims priority under 35 U.S.C. §119(a) on Patent Application No(s). 101224273 filed in Taiwan, R.O.C. on Dec. 14, 2012, the entire contents of which are hereby incorporated by reference.

BACKGROUND OF THE INVENTION

1. Field of the Invention

The present invention relates to the field of liquid nebulization devices, and more particularly to a constant quantity control nebulization device that controls the consumption of a liquid to be sprayed when a rotary method is used for switching the supply of the liquid to be nebulized for the nebulization and the spray of the liquid.

2. Description of the Related Art

In recent years, various types of nebulization devices are used extensively in different areas including medical healthcare and cosmetics. For example, a liquid such as the medicine or cosmetic solution is nebulized to form gas molecules used for maintaining or curing respiratory tract, improving human immunity, softening pores for an easy removal of dead skin cells and dirt, and supplementing water quickly to maintain skin smooth, clean and exquisite.

The operation principle of the nebulization devices is to generate vibration energy by a piezoelectric device, and then transmit the vibration energy to a spray orifice plate through a conduction plate in order to nebulize the liquid passing through the spray orifice plate and spray out the nebulized liquid. Therefore, the liquid including the medicine and cosmetic solutions can be nebulized to form small gaseous molecules to be absorbed by human body easily. Particularly, it is necessary to control the consumption of a medicine with a medical treatment effect effectively in order to avoid overdose and underdose that will affect the efficacy of the medical treatment.

At present a vast majority of the nebulization devices supplement the liquid to be nebulized by refilling, and the liquid consumption can be calculated by the time of using the nebulization device and the unit spray quantity of the nebulization device only. However, such method cannot control the consumption accurately, but just roughly estimates the consumption. In addition, the inventor of the present invention has filed a patent application for a disposable container that packages and prepares a liquid to be nebulized with a specific concentration ratio, wherein a seal film is covered onto an opening of the container, and the container comes with a one-time disposable design and is easy to store and carry. In addition, users can change a liquid to be nebulized anytime, and thus such container is very convenient. However, this kind of disposable containers is not designed with a one-time disposable according to the consumption, and the consumption cannot be controlled effectively. Obviously, the conventional disposable requires improvements.

SUMMARY OF THE INVENTION

In view of the problems of the prior art, it is a primary objective of the present invention to provide a constant quantity control nebulization device, wherein a fixing plate is combined with a main body to form a first liquid storage space with a predetermined volume, and a rotary ring is axially coupled to the fixing plate and sheathed on a container that contains a liquid to be nebulized, and a first through hole and a second through hole are formed between the rotary ring and the fixing plate, such that after the rotary ring is rotated, the liquid to be nebulized is filled up into the first liquid storage space, so that the nebulization device can control the consumption of the liquid accurately and improve the convenience of operation and use.

Another objective of the present invention is to provide a constant quantity control nebulization device, wherein the rotary ring has a seal film breaking structure for breaking a seal film at the container opening, so that the liquid to be nebulized can flow into the first liquid storage space successfully to improve the convenience of operation and use.

A further objective of the present invention is to provide a constant quantity control nebulization device, wherein the fixing plate has a start switch, and the rotary ring has a corresponding safety switch, such that when the rotary ring is rotated to open and interconnect the first through hole and the second through hole, the start switch and the safety switch are electrically disconnected and cannot supply electric power. When, the first through hole and the second through hole are closed and disconnected, the start switch and the safety switch are electrically conducted. Such arrangement can overcome the drawback of the conventional nebulization device that is unable to control the consumption due to erroneous operation, and also can improve the convenience of operation and use.

To achieve the aforementioned objectives, the present invention provides a constant quantity control nebulization device installed to a container that contains a liquid to be nebulized and has a seal film covered onto an opening of the container, comprising: a main body, having a containing space formed therein and a first liquid storage space of a predetermined volume formed at the top of the main body; an nebulization module, installed in the containing space, and interconnected to the first liquid storage space, and electrically coupled to a power supply; a fixing plate, fixed onto the main body, for sealing the first liquid storage space, and the fixing plate having a first through hole; and a rotary ring, having a first opening formed at the top of the rotary ring and a second opening formed at the bottom of the rotary ring, and a partition installed in the rotary ring, and the second opening being sheathed on the top of the main body and axially coupled to the fixing plate, and a second liquid storage space being defined between the first opening and the partition and corresponding to the container, and the partition having a seal film breaking element corresponding to the seal film and a second through hole corresponding to the first through hole; such that when use, the container is installed into the first opening, such that after the seal film breaking element cuts and breaks the seal film, the liquid to be nebulized flows into the second liquid storage space, and the rotary ring is rotated to align the first through hole and the second through hole with each other precisely, and then the liquid to be nebulized flows into the first liquid storage space, and the rotary ring can be rotated in an opposite direction to close the first liquid storage space, and the nebulization module releases, nebulizes and sprays the liquid to be nebulized with the predetermined volume.

Wherein, the fixing plate has a shaft hole formed at a center position of the fixing plate, and the rotary ring has a shaft disposed at a center position of the rotary ring and axially coupled into the shaft hole.

Wherein, the seal film breaking element includes a cutting portion and a prop rod, and the cutting portion is installed at a position of the partition adjacent to the rotary ring, and the prop rod is disposed onto a side corresponding to the second through hole. The prop rod props at the seal film, and the cutting portion cuts or scratches the seal film to let the liquid to be nebulized flow through successfully.

Wherein, the container opening has a protruding pillar installed at the exterior of the container opening, and the internal wall of the first opening has an embedding slot, and the protruding pillar is passed through and fixed into the embedding slot.

Wherein, a first sealing rubber ring is installed between the fixing plate and the rotary ring, and the partition periphery has a second sealing rubber ring, corresponding to the opening of the container, and the periphery of the second through hole has a water sealing portion tightly coupled to a side of the fixing plate to avoid contaminating the liquid to be nebulized that flows out and prevent leakage.

Wherein, the external periphery of the fixing plate has a plurality of positioning members and a plurality of snap-in members installed with an interval apart and staggered with one another, and the opening at the top of the main body has a plurality of positioning slots and a plurality of snap-in slots corresponding to the positioning members and the snap-in members respectively to fix the fixing plate onto the main body securely.

Wherein, the external periphery of the opening of the main body has a positioning column, and the rotary ring has a ring slot corresponding to the positioning column, and the main body has a position-limiting slot opposite to the other side of the positioning column, and the rotary ring has a bump opposite to the position-limiting slot. Therefore, the rotary ring can be latched onto the main body and will not fall off easily, and the bump and the position-limiting slot are provided for limiting the rotation range of the rotary ring.

Wherein, the partition has an arc-shaped position-limiting slot formed at the bottom of the partition, and the fixing plate has a position-limiting column corresponding to the position-limiting slot and movably installed in the position-limiting slot, for limiting the rotation of the rotary ring with respect to the fixing plate. Therefore, the rotation range of the rotary ring can be limited.

In a preferred embodiment of the present invention, the constant quantity control nebulization device further comprises a start switch electrically coupled between the nebulization module and the power supply, and the start switch is installed on an external wall of an opening of the main body and disposed on a side of the positioning column, and the internal wall of the second opening of the rotary ring is disposed on a side of the ring slot.

In addition, a safety switch is electrically coupled between the start switch and the power supply, and the safety switch is disposed at the bottom of the partition and the top of the fixing plate. The start switch is used for controlling the electric connection status of the nebulization module, and the safety switch is used for controlling the electric connection status of the start switch. Therefore, the invention can overcome the problem of erroneous operation when the rotary ring is installed or rotated, or even when the nebulization module is turned on.

DETAILED DESCRIPTION OF THE PREFERRED EMBODIMENTS

The technical content of the present invention will become apparent with the detailed description of preferred embodiments and the illustration of related drawings as follows.

Figure 1:
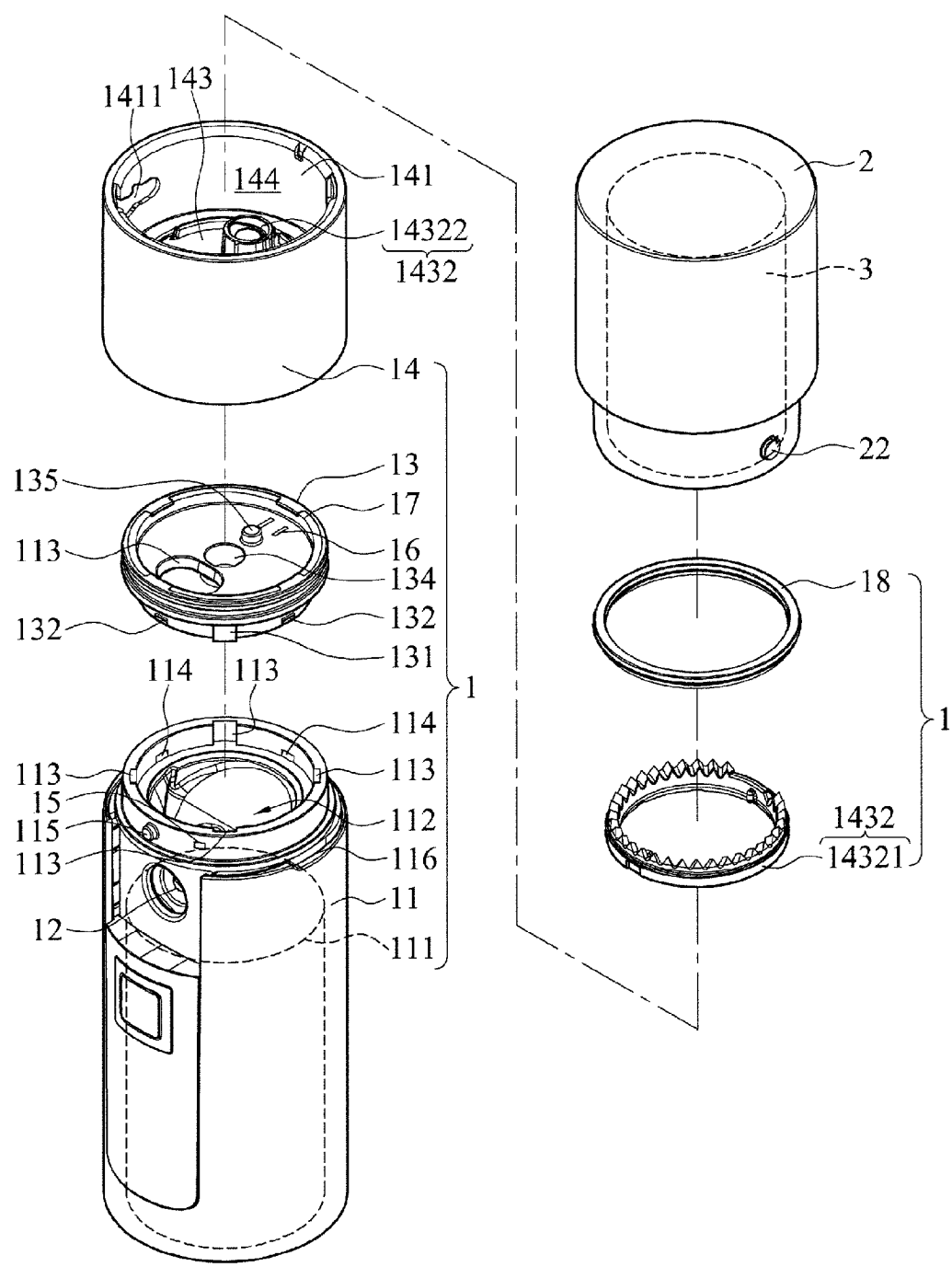
FIG. 1 is an exploded view of a constant quantity control nebulization device of a preferred embodiment of the present invention, viewing from the top side of the device.
Figure 2:
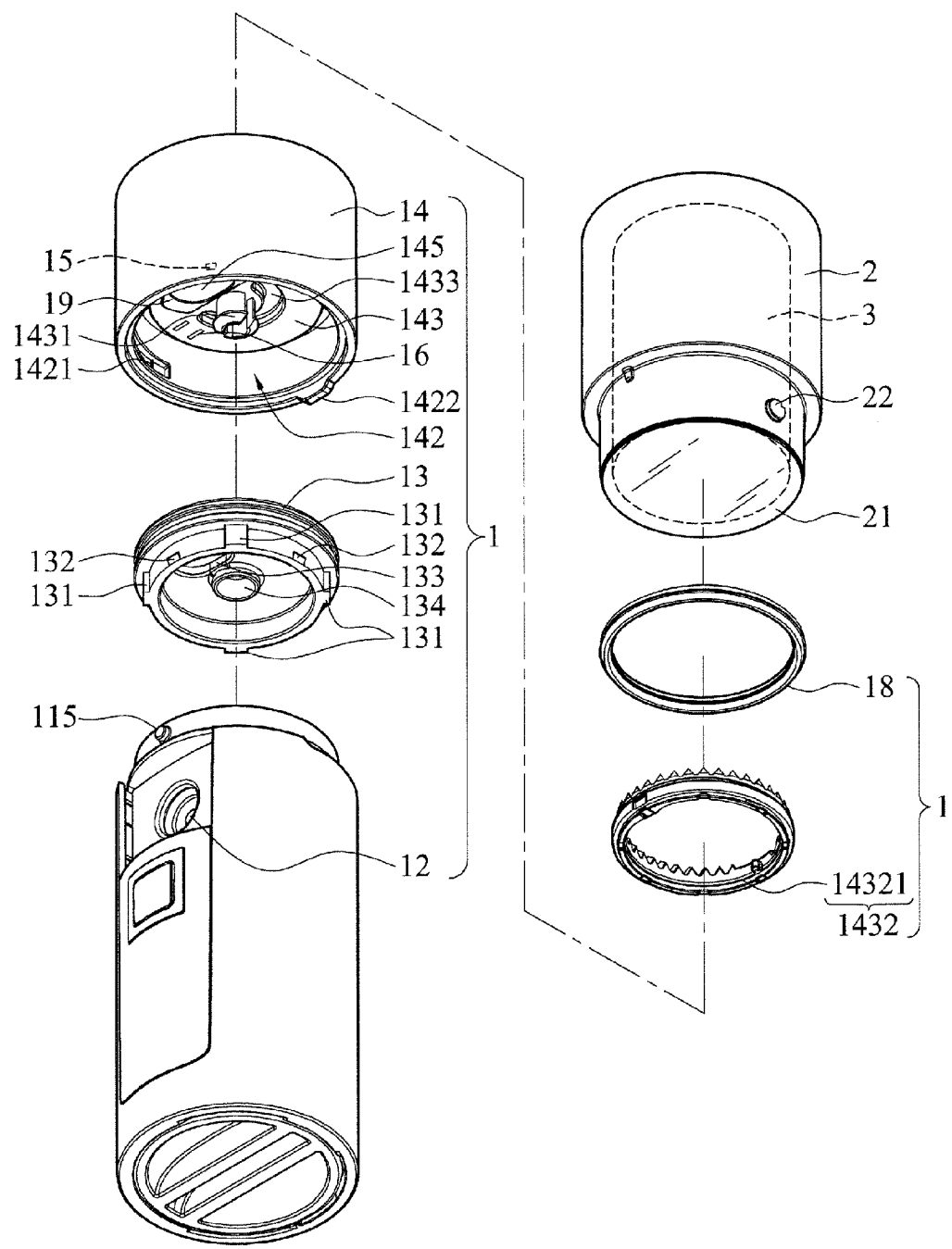
FIG. 2 is an exploded view of a constant quantity control nebulization device of a preferred embodiment of the present invention, viewing from the bottom side of the device.
Figure 3:
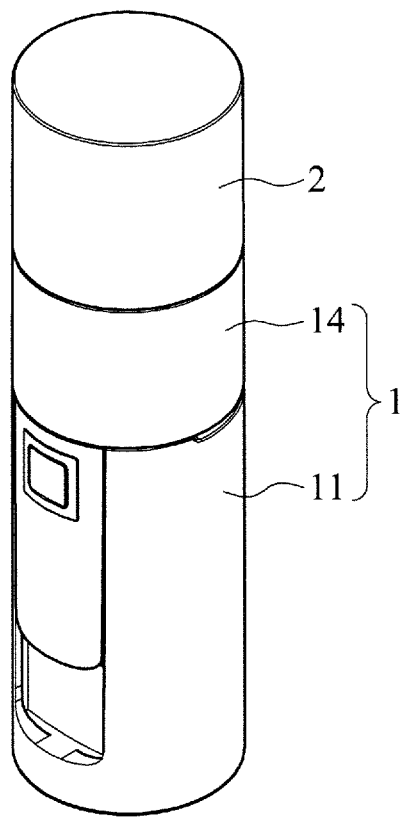
FIG. 3 is a perspective view of a constant quantity control nebulization device of a preferred embodiment of the present invention.
Figure 4:
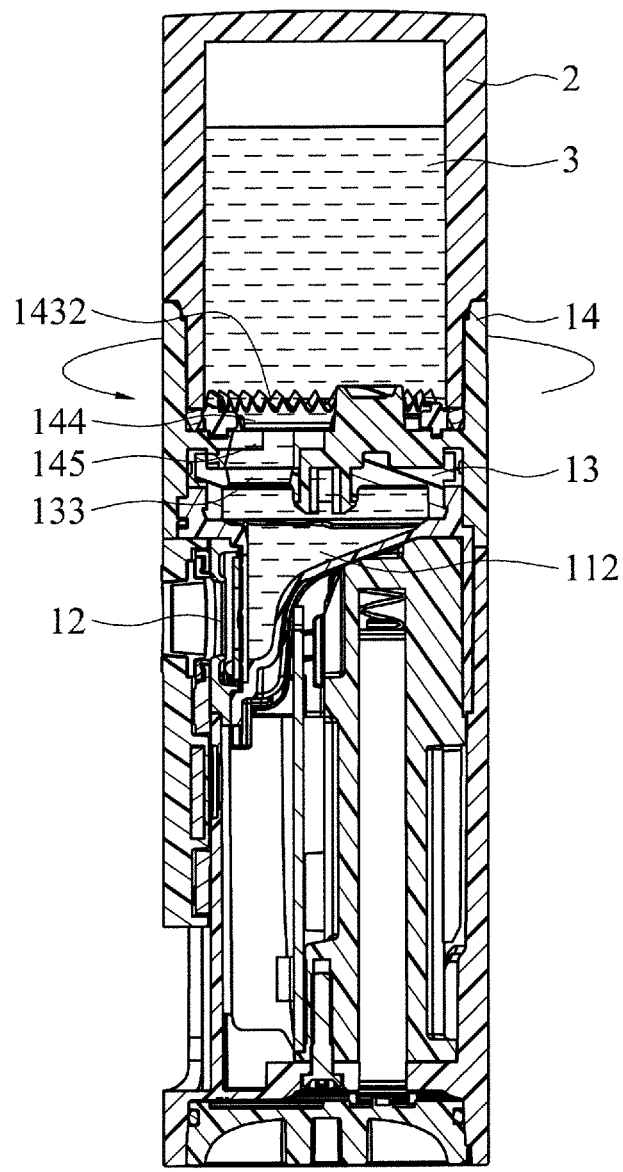
FIG. 4 is a first schematic view of the using status of a constant quantity control nebulization device of a preferred embodiment of the present invention.
Figure 5:
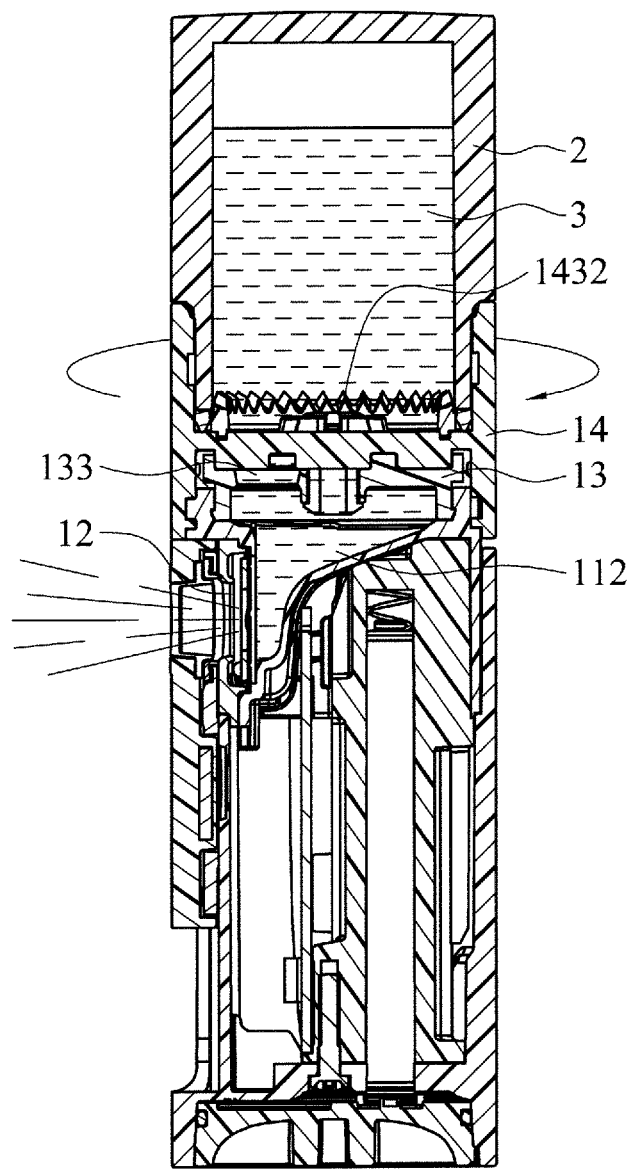
FIG. 5 is a second schematic view of the operation of a constant quantity control nebulization device of a preferred embodiment of the present invention.

With reference to FIGS. 1 to 5 for the exploded views of a preferred embodiment of the present invention viewing from different angles, a perspective view and schematic views of the application statuses of a constant quantity control nebulization device of a preferred embodiment of the present invention respectively, the constant quantity control nebulization device 1 is installed to a container 2 that contains a liquid to be nebulized 3 and has a seal film 21 covered onto an opening of the container 2 and a protruding pillar 22 disposed outside the container. The constant quantity control nebulization device 1 comprises a main body 11, an nebulization module 12, a fixing plate 13 and a rotary ring 14.

The main body 11 is a circular cylindrical structure and includes a containing space 111 therein, and the top of the main body 11 has a first liquid storage space 112 with a predetermined volume. It is noteworthy that the predetermined volume of the first liquid storage space 112 is set to a level corresponsive to the consumption of the liquid to be nebulized 3, and designers can change the predetermined volume of the liquid to be nebulized 3. Further, a plurality of positioning slots 113 and a plurality of snap-in slots 114 are formed at the opening at the top of the main body 11, and the positioning slot 113 and the snap-in slots 114 are disposed with an interval apart and staggered with one another. Further, a positioning column 115 is disposed at the external periphery of the opening of the main body 11, and a position-limiting slot 116 opposite to the other side of the positioning column 115.

The nebulization module 12 is installed in the containing space 111, interconnect to the first liquid storage space 112, and electrically coupled to a power supply (not shown in the figure) for driving the nebulization module 12 to nebulize the liquid to be nebulized 3 and sprays the nebulized liquid to be nebulized 3.

The fixing plate 13 is a circular disk structure having a plurality of positioning members 131 and a plurality of snap-in members 132 disposed with an interval apart at the external periphery of the fixing plate 13 and staggered with each other for a positioning purpose and latched and snapped into the positioning slot 113 and the snap-in slots 114 to seal the first liquid storage space 112. A first through hole 133 is formed on the fixing plate 13, and a shaft hole 134 is formed at a center position of the fixing plate. It is noteworthy that designers can increases the thickness at a position where the bottom of the fixing plate 13 is coupled to the first liquid storage space 112 in order to adjust the predetermined volume of the first liquid storage space 112. If the thickness of the bottom of the fixing plate 13 increases, the predetermined volume will decrease, and so forth. If the thickness of the bottom of the fixing plate 13 decreases, the predetermined volume will increase.

In addition, the rotary ring 14 is a circular cylindrical structure with a shape corresponding to that of the main body 11, and the rotary ring 14 has a first opening 141 formed at the top of the rotary ring 14 and a second opening 142 formed at the bottom of the rotary ring 14, and the rotary ring 14 includes a partition 143 installed therein. Wherein, an embedding slot 1411 is formed an internal wall on of the first opening 141, and the protruding pillar 22 is passed into the embedding slot 1411 to fix the container 2 with the rotary ring 14, and a second liquid storage space 144 is defined between the first opening 141 and the partition 143 and corresponding to the container 2. The second opening 142 is sheathed on the top of the main body 11, and a ring slot 1421 is formed on an internal wall of the second opening 142 and corresponding to the positioning column 115, and a bump 1422 is disposed on the other side and corresponding to the position-limiting slot 116. The partition 143 has a shaft 1431 disposed at a center position of the bottom of the partition 143 and axially coupled into the shaft hole 134. The partition 143 also has a seal film breaking element 1432 disposed at the top of the partition 143 and corresponding to the seal film 21. The partition further has a second through hole 145 corresponding to the first through hole 133. In addition, the seal film breaking element 1432 includes a cutting portion 14321 and a prop rod 14322, and the cutting portion 14321 is disposed at the partition 143 and adjacent to the rotary ring 14, and the prop rod 14322 is installed onto a side of the second through hole 145. To further improve the position limiting effect for the rotation of the rotary ring 14, the bottom of the partition 143 has an arc-shaped position-limiting slot 1433, and top of the fixing plate 13 has a position-limiting column 135 corresponding to the position-limiting slot 1433, and the position-limiting column 135 is movably installed in the position-limiting slot 1433 for limiting the rotation of the rotary ring 14 with respect to the fixing plate 13.

In addition, the constant quantity control nebulization device 1 of the present invention further comprises a start switch 15 and a safety switch 16, electrically coupled between the nebulization module 12 and the power supply, and the start switch 15 is installed on an external wall of an opening of the main body 11 and disposed on a side of the positioning column 115 and an internal wall of the second opening 142 of the rotary ring 14 and disposed on a side of the ring slot 1433. The safety switch 16 is electrically coupled between the start switch 15 and the power supply, and the safety switch 16 is installed at the bottom of the partition 143 and the top of the fixing plate 13 separately. The start switch 15 controls the electric connection status of the nebulization module 12, and the safety switch 16 controls the electric connection status of the start switch 15, so that if the safety switch 16 is electrically disconnected (while installing the rotary ring 14 or rotating the rotary ring), the start switch 15 and the nebulization module 12 will also be electrically disconnected and cannot be operated. If the safety switch 16 is electrically conducted and the start switch 15 is electrically disconnected, the nebulization module 12 will be electrically disconnected and cannot be operated. Only if both of the safety switch 16 and the start switch 15 are electrically conducted at the same time, the nebulization module 12 will be operated successful. The double-safety operation design can avoid users' erroneous operation effectively.

To waive a first sealing rubber ring 17 installed between the fixing plate 13 and the rotary ring 14, the partition 143 has a second sealing rubber ring 18 formed at the periphery of the partition 143 and corresponding to an opening of the container 2, and the second through hole 145 has a water sealing portion 19 disposed at the periphery of the second through hole 145 and tightly coupled to a side of the fixing plate 13.

With reference to FIGS. 4 and 5 together with FIGS. 1 and 2, the container 2 is installed inside the first opening 141 for the use of the constant quantity control nebulization device. After the seal film breaking element 142 cuts the seal film 21, the liquid to be nebulized 3 flows into the second liquid storage space 144. The rotary ring 14 can be rotated to align the first through hole 133 with the second through hole 145 precisely to let the liquid to be nebulized 3 flow into the first liquid storage space 112, and the start switch 15 and the safety switch 16 are electrically disconnected. After the first liquid storage space 112 is filled up with the liquid to be nebulized 3, the rotary ring 14 can be rotated in an opposite direction till the first through hole 133 and the second through hole 145 are staggered with each other to close the first liquid storage space 112, and the start switch 15 and the safety switch 16 are electrically conducted to drive the nebulization module 12 to release, nebulize and spray the liquid to be nebulized 3 of the predetermined volume.

What is claimed is:

1. A constant quantity control nebulization device, installed to a container that contains a liquid to be nebulized and has a seal film covered onto an opening of the container, comprising:

a main body, having a containing space formed therein and a first liquid storage space of a predetermined volume formed at the top of the main body;

an nebulization module, installed in the containing space, and interconnected with the first liquid storage space, and electrically coupled to a power supply;

a fixing plate, fixed onto the main body, for sealing the first liquid storage space, and the fixing plate having a first through hole; and a rotary ring, having a first opening formed at the top of the rotary ring and a second opening formed at the bottom of the rotary ring, and a partition installed in the rotary ring, and the second opening being sheathed on the top of the main body and axially coupled to the fixing plate, and a second liquid storage space being defined between the first opening and the partition and corresponding to the container, and the partition having a seal film breaking element corresponding to the seal film and a second through hole corresponding to the first through hole;

such that when use, the container is installed into the first opening, such that after the seal film breaking element cuts and breaks the seal film, the liquid to be nebulized flows into the second liquid storage space, and the rotary ring is rotated to align the first through hole and the second through hole with each other, and then the liquid to be nebulized flows into the first liquid storage space, and the rotary ring can be rotated in an opposite direction to close the first liquid storage space, and the nebulization module releases, nebulizes and sprays the liquid to be nebulized with the predetermined volume.

2. The constant quantity control nebulization device of claim 1, wherein the container opening has a protruding pillar installed at the exterior of the container opening, and the internal wall of the first opening has an embedding slot, and the protruding pillar is passed through and fixed into the embedding slot.

3. The constant quantity control nebulization device of claim 1, wherein the fixing plate has a shaft hole formed at a center position of the fixing plate, and the rotary ring has a shaft disposed at a center position of the rotary ring and axially coupled into the shaft hole.

4. The constant quantity control nebulization device of claim 2, further comprising a first sealing rubber ring installed between the fixing plate and the rotary ring, and the partition periphery has a second sealing rubber ring, corresponding to the opening of the container, and the periphery of the second through hole has a water sealing portion tightly coupled to a side of the fixing plate.

5. The constant quantity control nebulization device of claim 3, wherein the seal film breaking element includes a cutting portion and a prop rod, and the cutting portion is installed at a position of the partition adjacent to the rotary ring, and the prop rod is disposed correspondingly onto a side of the second through hole.

6. The constant quantity control nebulization device of claim 4, wherein the external periphery of the fixing plate has a plurality of positioning members and a plurality of snap-in members installed with an interval apart and staggered with one another, and the opening at the top of the main body has a plurality of positioning slots and a plurality of snap-in slots corresponding to the positioning members and the snap-in members respectively.

7. The constant quantity control nebulization device of claim 5, wherein the container opening has a protruding pillar installed at the exterior of the container opening, and the internal wall of the first opening has an embedding slot, and the protruding pillar is passed through and fixed into the embedding slot.

8. The constant quantity control nebulization device of claim 6, wherein the external periphery of the opening of the main body has a positioning column, and the rotary ring has a ring slot corresponding to the positioning column, and the main body has a position-limiting slot opposite to the side of the positioning column, and the rotary ring has a bump opposite to the position-limiting slot.

9. The constant quantity control nebulization device of claim 7, further comprising a first sealing rubber ring installed between the fixing plate and the rotary ring, and the partition periphery has a second sealing rubber ring, corresponding to the opening of the container, and the periphery of the second through hole has a water sealing portion tightly coupled to a side of the fixing plate.

10. The constant quantity control nebulization device of claim 8, wherein the partition has an arc-shaped position-limiting slot formed at the bottom of the partition, and the fixing plate has a position-limiting column corresponding to the position-limiting slot and movably installed in the position-limiting slot, for limiting the rotation of the rotary ring with respect to the fixing plate.

11. The constant quantity control nebulization device of claim 9, wherein the external periphery of the fixing plate has a plurality of positioning members and a plurality of snap-in members installed with an interval apart and staggered with one another, and the opening at the top of the main body has a plurality of positioning slots and a plurality of snap-in slots corresponding to the positioning members and the snap-in members respectively.

12. The constant quantity control nebulization device of claim 10, further comprising a start switch electrically coupled between the nebulization module and the power supply, and the start switch being installed on an external wall of an opening of the main body and disposed on a side of the positioning column, and the internal wall of the second opening of the rotary ring being disposed on a side of the ring slot.

13. The constant quantity control nebulization device of claim 11, wherein the external periphery of the opening of the main body has a positioning column, and the rotary ring has a ring slot corresponding to the positioning column, and the main body has a position-limiting slot opposite to the side of the positioning column, and the rotary ring has a bump opposite to the position-limiting slot.

14. The constant quantity control nebulization device of claim 12, further comprising a safety switch electrically coupled between the start switch and the power supply, and the safety switch being disposed at the bottom of the partition and the top of the fixing plate.

15. The constant quantity control nebulization device of claim 13, wherein the partition has an arc-shaped position-limiting slot formed at the bottom of the partition, and the fixing plate has a position-limiting column corresponding to the position-limiting slot and movably installed in the position-limiting slot, for limiting the rotation of the rotary ring with respect to the fixing plate.

16. The constant quantity control nebulization device of claim 15, further comprising a start switch electrically coupled between the nebulization module and the power supply, and the start switch being installed on an external wall of an opening of the main body and disposed on a side of the positioning column, and the internal wall of the second opening of the rotary ring being disposed on a side of the ring slot.

17. The constant quantity control nebulization device of claim 16, further comprising a safety switch electrically coupled between the start switch and the power supply, and the safety switch being disposed at the bottom of the partition and the top of the fixing plate.

* * * * *